(12) United States Patent
Baudry et al.

(10) Patent No.: US 7,332,353 B2
(45) Date of Patent: Feb. 19, 2008

(54) METHOD FOR DETECTING ANALYTE(S) USING MAGNETIC COLLOIDAL PARTICLES

(75) Inventors: Jean Baudry, Paris (FR); Jérôme Bibette, 4 rue Malebranche, 75011 Paris (FR); Alain Rousseau, Paris (FR)

(73) Assignees: Diagnostica Stago (FR); Jérôme Bibette (FR)

( * ) Notice: Subject to any disclaimer, the term of this patent is extended or adjusted under 35 U.S.C. 154(b) by 204 days.

(21) Appl. No.: 10/496,114

(22) PCT Filed: Nov. 20, 2002

(86) PCT No.: PCT/FR02/03974

§ 371 (c)(1),
(2), (4) Date: Oct. 5, 2004

(87) PCT Pub. No.: WO03/044532

PCT Pub. Date: May 30, 2003

(65) Prior Publication Data

US 2005/0048673 A1   Mar. 3, 2005

(30) Foreign Application Priority Data

Nov. 20, 2001   (FR) .................................. 01 15011

(51) Int. Cl.
*G01N 33/553* (2006.01)
(52) U.S. Cl. ..................................... 436/526
(58) Field of Classification Search ................ 436/526, 436/514, 517, 518, 523, 524, 525, 527, 172, 436/149; 435/4, 7.1, 7.91–7.95, 287.1–287.3; 422/73
See application file for complete search history.

(56) References Cited

U.S. PATENT DOCUMENTS

| 4,127,385 | A | * | 11/1978 | Weeke ........................ 436/524 |
| 4,554,088 | A | * | 11/1985 | Whitehead et al. ...... 252/62.54 |
| 4,622,298 | A | * | 11/1986 | Mansour et al. .............. 435/34 |
| 5,298,741 | A | * | 3/1994 | Walt et al. ............. 250/227.23 |
| 5,512,332 | A | | 4/1996 | Liberti et al. |
| 5,637,469 | A | * | 6/1997 | Wilding et al. ............ 435/7.21 |
| 5,776,706 | A | | 7/1998 | Siiman et al. |
| 5,817,458 | A | | 10/1998 | King et al. |
| 6,268,222 | B1 | * | 7/2001 | Chandler et al. ........... 436/523 |
| 6,440,725 | B1 | * | 8/2002 | Pourahmadi et al. .... 435/288.5 |
| 6,548,311 | B1 | * | 4/2003 | Knoll ......................... 436/524 |

FOREIGN PATENT DOCUMENTS

| WO | WO-94/09368 | 4/1994 |
| WO | WO-97/20214 | 6/1997 |
| WO | WO-98/16101 | 4/1998 |
| WO | WO-98/51435 | 11/1998 |

* cited by examiner

*Primary Examiner*—Ann Y. Lam
(74) *Attorney, Agent, or Firm*—Stites & Harbison PLLC; Marvin Petry

(57) ABSTRACT

The invention concerns a method for detecting and/or quantifying at least an analyte in a liquid medium, characterized in that it consists in using magnetic colloidal particles functionalized at the surface with at least a ligand specific of the analyte to be detected and/or assayed and in that it comprises: contacting said particles with said medium to be analyzed; applying a magnetic field to said medium, at an intensity sufficient to cause said magnetic particles to be structured in the form of chains; maintaining said magnetic field for a sufficient time interval to enable coupling or combination of the analyte concerned with at least two specific ligands present respectively on two neighbouring particles of a chain; cancelling the magnetic field, and determining the presence and/or absence of said analyte and, as the case may be, its concentration via the presence and/or the absence of said permanent chains of magnetic particles.

24 Claims, 3 Drawing Sheets

METHOD FOR DETECTING ANALYTE(S) USING MAGNETIC COLLOIDAL PARTICLES

FIELD OF THE INVENTION

The present invention relates to method which is useful for detecting at least one analytical species in a liquid, biological or synthetic sample, and which involves the coupling of this species with a reagent analogous to an agglutinating reagent.

BACKGROUND OF THE INVENTION

To date, many "agglutination" methods have already been proposed. They are mainly used for detecting antigens and/or antibodies for diagnostic purposes. These methods are in particular applied for bioassays (pregnancy tests, clotting tests) or the diagnosis of infectious diseases. However, these methods generally have a limited sensitivity. In fact, the general principle of these tests consists in detecting the formation of a gel of colloidal particles which forms in the presence of the analyte. In this type of test, the analyte must be able to attach two colloidal particles, the surfaces of which are covered with a molecule which recognizes, in the broadest sense, the analyte to be assayed.

SUMMARY OF THE INVENTION

The present invention is based more particularly on the use of magnetic particles as colloidal agglutinating reagents.

Magnetic particles are already used in biological separation techniques or diagnostic test techniques (WO 94/09368; EP 180 384; WO 98/51435). Magnetic separations are found to be rapid and easy to implement and require simplified equipment. Using magnetic particles covered with a molecule which recognizes the analyte to be captured, it is possible to separate the analyte in question from a complex mixture, under the effect of magnetic forces. This approach is used to advantage in the "ELISA" assay (Enzyme Linked Immunoassay), for example. The magnetic particles used incorporate a magnetic material, namely, for example, magnetite, ferrite, chromium oxide or nickel oxide, in a matrix, generally organic in nature. They are functionalized at the surface with reactive groups of the antigen, haptene or antibody type, intended to react with the active species to be separated.

In order to avoid the problems associated with magnetic remanence, a superparamagnetic material is generally preferred to conventional ferromagnetic material. Ferrofluids, which possess a high magnetization and saturation (greater than 100 mT) and do not show any magnetic remanence in the absence of an external magnetic field, are good candidates for being integrated into protocols for preparing superparamagnetic colloids.

As regards the present invention, it aims to take advantage of the ability shown by these magnetic colloids to adopt a specific structural organization under the effect of a magnetic field.

In this instance, agglutination induced by the field produces, depending on the fraction of colloids by volume, isolated "chains" or groups of chains called "clusters". Chains or clusters will hereinafter be referred to indifferently as chains. Detailed documentation on these structures and their formation will be found in many publications.

In other words, in the absence of a magnetic field, the particles are in a dispersed form. In the presence of a magnetic field, they become organized to form chains of particles in aqueous solution. These chains are, of course, reversible and are rapidly undone when the magnetic field is removed, under the effect of thermal agitation. Advantageously, if these particles are sufficiently small, and therefore Brownian and polarizable, these chains form rapidly along the axis of the field which is applied to them and are not sensitive to gravity. This phenomenon is illustrated diagrammatically in FIG. 1A. FIG. 1B shows a micrograph of the chains formed by such particles in a magnetic field.

Unexpectedly, the inventors have demonstrated that it is possible to exploit this ability of magnetic colloidal particles to rapidly become organized in chains of particles under the effect of a magnetic field, for the purposes of detecting and/or quantifying specific species(s) in a liquid medium.

In this instance, when these magnetic colloidal particles are covered at the surface with specific ligands and when the continuous phase, in which they are dispersed, contains a species capable of reacting with at least two specific ligands, the magnetic field will catalyze the attachment of the species concerned to two distinct and neighboring particles in the chain induced by the magnetic field. After the magnetic field has been removed, the particles to which the species has attached remain organized in permanent chains and thus indicate the presence of the targeted species in the medium analyzed.

More precisely, the present invention aims first of all at a method for detecting and/or quantifying at least one analyte in a liquid medium, characterized in that it uses magnetic colloidal particles functionalized at the surface with at least one ligand specific for an analyte to be detected and/or assayed and in that it comprises:

1. bringing said particles into contact with said medium,
2. applying a magnetic field to said medium, at a strength sufficient to cause said magnetic particles to be structured in the form of chains,
3. maintaining this magnetic field for a period of time sufficient to enable coupling or combination of the analyte concerned with at least two specific ligands present respectively on two neighboring particles of a chain,
4. removing the magnetic field, and
5. determining the presence and/or absence of said analyte and, where appropriate, its concentration by the presence or absence of permanent chain(s) of magnetic colloidal particles in said liquid medium.

It should be noted that the order in which these steps are listed corresponds to a preferred embodiment of the invention, but that it is also possible, in the context of this invention, to carry them out in a different order, for example by activating the magnetic field before introducing the medium to be analyzed.

In the context of the invention, it is also possible to collect the magnetic colloidal particles linked by the analyte intended to be detected, assayed or displaced.

In the context of the invention, it is also possible to use very diverse field and field gradient geometries, and also very diverse "agglutination cells" geometries. These variations are, depending on the case, liable to optimize both the rapidity of the ligand-receptor association and the detection of the permanent chains, which may be very variable in length and thickness depending on the conditions. In particular, the invention encompasses the microfluid devices which are such that the width or the height of the channels is less than 100 μm. Fields oriented perpendicular or parallel to the axis of the channel can be used.

Advantageously, the method is implemented in diagnostic tools, such as analytical devices. Automated analytical devices are particularly preferred.

As regards more particularly the characterization of the permanent chains, it may advantageously be carried out by simple microscopic examination of the medium analyzed. However, in particular when an automated analytical device is used, it is preferable to detect the presence of the chains optically. It is thus possible to detect the presence of chains by measuring light scattering, for example by photometry or turbidimetry. Another variant constitutes the processing of the image captured, for example, by a CCD camera. This variant has the advantage of enabling a fine analysis of the size of the chains. Any appropriate light source, preferably a laser, can be used for these detection variants.

Of course, the formation of the chains, comparable to conventional agglutinates, depends, firstly, on the concentration of the analyte in the medium analyzed and, secondly, on the concentration of particles. Diagrammatically, it may be considered that the more analyte there is present in said medium, the longer the chains, and the higher the concentration of particles, the thicker the chains will be and the more comparable to aggregates. In the context of the present invention, it thus proves to be possible to determine the concentration of analyte from the quantification of the density of magnetic particles organized in the form of (a) permanent chain(s). This density measurement can be made by conventional techniques. A reference calibration can thus be established beforehand for a given analyte.

The method claimed is particularly advantageous in terms of sensitivity. It thus proves to be advantageous for detecting analytes at low concentrations in liquid media.

As is shown in the example below, the chains persist for concentrations of analytes, in this instance of antigens, of the order of $10^{-9}$ mol/l versus $10^{-5}$ mol/l for a conventional agglutination assay, carried out with the same ligand-receptor couple (biotin-streptavidin). Advantageously, this concentration threshold is lower than the concentration threshold necessary for the persistence of aggregates or the formation of a gel as expected in a conventional agglutination assay, carried out with the same antigen-antibody couple, and in the absence of a magnetic field.

The method claimed can therefore advantageously substitute for a conventional agglutination assay, and greatly increase the sensitivity of the assay.

For the purposes of the present invention, the term "colloidal" means that the particles are between 5 and 10 000 nm, and more preferably between 100 and 500 nm, in size. However, it is particularly advantageous to favor the use of particles which are as small as possible while at the same time guaranteeing that they have a sufficient magnetic susceptibility to permit immediate agglutination under the conjugated action of the magnetic dipolar forces and of the Brownian movement. Generally, this compromise is reached for particle diameters of no more than a few microns, and preferably of approximately 0.1 to 0.5 micron, when the amount of magnetic material, generally encapsulated iron oxide, is at a maximum.

For the reasons mentioned above, the use of superparamagnetic colloidal particles is preferred.

Several different kinds of technology exist for producing superparamagnetic colloidal particles having the required qualities relative to the invention. These are, for example, techniques for coprecipitation of a natural or synthetic polymer material with an aqueous ferrofluid, or for emulsification with a ferrofluid in organic phase.

The preferred technology for obtaining this type of colloidal material in a controlled manner is based on a principle of emulsification followed by polymerization and grafting protocols. These emulsions can in particular be produced by shearing of a mixture consisting of an organic ferrofluid and an aqueous phase rich in surfactant. The ferrofluid is chosen so that its organic phase is slightly soluble in the aqueous phase. In this instance, each droplet is converted into a spherical conglomeration of nanometric particles of the magnetic material concerned, preferably magnetic iron oxide (maghemite) with approximately 60% by volume of iron oxide in each droplet. The particles thus obtained are then polymerized by introducing a hydrophobic monomer such as styrene, so that the reaction takes place in the droplets. The introduction of water-soluble functional monomers at the end of polymerization provides functionalization of the surfaces. These two operations together, namely emulsification and polymerization, result in spherical particles which are very rich in iron oxide and coated with a polymerized and functionalized layer. For the preparation of this emulsion, reference may in particular be made to the procedure published by J. Bibette in J. Magn. and Magn. Mat. V. 122, p. 37 (1993) and by T. Mason and J. Bibette in Phys. Rev. Lett. 77, 3481 (1996) and in WO 97/38787 and FR 2800836.

Advantageously, the magnetic material incorporated is chosen from iron oxides, cobalt oxides or finally divided and stabilized metals, and is preferably maghemite. It is incorporated into the particles at a rate of 40% by volume, and preferably of 60%. According to a preferred variant of the invention, the basic magnetic material is a ferrofluid.

The magnetic colloidal particles thus obtained are particularly advantageous insofar as they are compatible with the immobilization, at their surface, of a large number of ligands, according to conventional industrial methods.

Advantageously, they can be combined with a large variety of the specific ligands so as to convert them into reagents used in particular for immunoassays and agglutination assays as described in the present invention.

The molecules termed ligands can be immobilized at the surface of the magnetic colloidal particles by adsorption interactions, covalent interactions and/or high affinity interactions.

The covalent coupling can, for example, be carried out using chemical reactive groups present at the surface of the particles. By way of illustration of these groups, mention may more particularly be made of carboxyl, amino, aldehyde and epoxy groups. When an analyte intended to be characterized is a reactive chemical species, these groups are themselves capable of performing the role of the ligand specific for the targeted analyte.

As regards the immobilization resulting from a high affinity interaction, it is generally mediated by two partners of a high affinity binding couple, such as (poly)carbohydrates/electin, biotin or biotinylated compounds/avidin or streptavidin, protein receptor and its specific ligand, haptene/antibody, etc.

Finally, the attachment of the ligand to the surface of the particles can be carried out either directly or using spacer elements, also referred to using the terms "linker" or "spacer".

These covalent or high affinity interactions make it possible to immobilize natural or synthetic ligands, such as, for example, peptides, proteins, including glycoproteins, lipoproteins and other similar or derived structures, in free or complex form, immunoglobins, nucleic acids such as DNA or RNA and their homologs, saccharides such as monosaccharides or bisaccharides, oligosaccharides and polysaccharides, lipids, hormones, receptors, metabolites or other biological substances.

The analytes that can be detected and/or assayed by the method claimed are preferably substances which can interact specifically and with high affinity with the functionalized particles of the present invention. They may thus be antigens and antibodies which can be determined by an immunoreaction, or nucleic acids which can be detected by a hybridization reaction, and more generally all types of proteins.

Preferably, the analytes possess a coefficient of diffusion within the medium to be analyzed which is at least equal to that of said particles.

The analyte to be identified may, in its natural form, react with two different ligands, in the same way, for example, as antigens and antibodies, which commonly offer several association sites.

In the opposite case, the medium to be analyzed is pretreated, prior to carrying out the method claimed, in order to make the analyte being sought reactive with respect to at least two molecules of one of its specific ligands. This type of pretreatment may in particular consist of functionalization of the analyte with at least one molecule of one of the partners of the "high affinity" couples discussed above. The carrying out of this type of pretreatment is within the competence of those skilled in the art.

A first embodiment of the invention concerns the detection and/or the quantification of (an) analyte(s) of the antibody type in a liquid sample, for example antibodies directed against pathogens such as viruses, bacteria or protozoa and other infectious agents, antibodies directed against tumors, antibodies directed against allergens, or autoantibodies.

A second embodiment of the invention concerns the detection and/or the quantification of antigens such as free antigens, for instance blood proteins and factors, such as clotting factors, metabolites, hormones, mediators, etc., or antigens attached to supports, for instance surface antigens of microorganisms, membrane-bound receptors, blood group antigens and antigens of the major histocompatibility system, etc.

The method claimed can also be used for detecting and/or quantifying nonbiological molecules such as, for example, any natural or artificial drug, it being understood that the drug in question may directly possess a double affinity for a ligand. Should this not be the case, a pretreatment will, by association, be necessary to make this type of analyte bivalent with respect to the designated ligand. This invention may in particular be advantageous in analytical and microanalytical chemistry.

According to a particular variant of the invention, several types of magnetic colloidal particles can be used in the same assay as agglutinating reagents. This can be advantageous when the analyte is readily reactive on two types of ligand. Moreover, the colloidal particles used according to the invention can carry a secondary label.

This labeling may be advantageous insofar as it may make it possible to combine a second mode of detection with the microscopic mode of detection, or simply to improve the microscopic detection. It is possible that this supplementary label may in particular be characterized visually, optically, mechanically and/or electrically. According to this variant of the invention, the characterization of the chains can be carried out directly by visualization under a microscope and indirectly by an optical, mechanical and/or electrical method according to the nature of the label selected. By way of illustration of the labels suitable for the invention, mention may in particular be made of color pigments, fluorescence agents or phosphorescence agents.

The liquid media analyzed can be synthetic or natural, such as for example biological fluids. They may in particular be body fluids such as, for example, blood (whole or fractionated), serum, plasma, saliva, urine or cerebrospinal fluid, used in diluted or undiluted form.

As regards the magnetic field, it may be created by various means which are known to those skilled in the art, for example Helmholtz coils, electromagnets or permanent magnets.

The continuous magnetic field applied is generally between 1 and 500 mT, preferably from 1 to 100 mT.

It is generally advantageous to apply a magnetic field which is essentially uniform. A simple means of producing such a field is to place, on either side of the "agglutination" zone, two poles, respectively North and South, of a permanent magnet or of an electromagnet. Another means consists in constructing a channel with an axis which is essentially circular and concentric with a Helmholtz coil magnetized by a current generator.

According to a preferred embodiment of the invention, an oscillating (alternating) magnetic field is applied.

The oscillation of the magnetic field makes it possible to increase the probability that an analyte to be assayed is in the vicinity of two specific ligands present, respectively, on two particles. At each field cycle, the particles can associate with one another in order to form or to extend the chains, without affecting the chains already formed. This means therefore makes it possible to complete the reaction between the ligands of the functionalized magnetic colloidal particles and the analyte to be assayed.

It is thus possible to assay lower concentrations of analyte and thus to obtain an assay with better sensitivity.

It should be noted, however, that some uses of the invention may require a non-uniform field. Specifically, the use of both a field capable of providing agglutination of the particles and a field gradient capable of concentrating the chains at a precise place may be sought. Both the field and its gradient may be manipulated simultaneously or separately. Thus, it is possible to first concentrate the analytes, and then to visualize them by the formation of aggregates of a sufficient size. In other applications which are part of the context of the invention, it will be preferable to perform the agglutination in a microfluid channel. It is known, for example (E. M. Lawrence et al., Int. J. of Modern Phys. B, 8, 2765-2777, 1994), that the diameter and the spacing of the columns or chains rich in magnetic particles depend on the magnetic field and on the thickness of the cell. It is thus possible to select agglutination conditions which are the most suitable for the application envisaged.

The means of introducing the medium to be analyzed may consist:
- of one or more notches or "wells" in which the sample is deposited, as in gel electrophesis "Electrophoresis: theory, techniques and biochemical and clinical applications, A. T. Andrews, Oxford University Press, NY 1986",
- or else of an overpressure or reduced pressure system as in capillary electrophoresis, see, for example "Capillary Electrophoresis", P. D. Grossman, J. C. Colburn published by Academic Press, San Diego, Calif., USA, 1992),
- or else of a channel via which a trickle of sample is continuously runout, as in electrophoresis in liquid vein, or else of one of the methods of introducing samples used in chromatography ("Chromatographie en phase liquide et supercritique" [Liquid chromatography and supercritical fluid chromatography], R. Rosset, M. Caude, A. Jardy, published by Masson, Paris 1991; "Practical High Performance Liquid Chromatography", V. R. Meyer, published by John Wiley, Chichester, N.Y., USA; "Chromatography of polymers", T. Prodver, published by ACS publ., Washington D.C., 1993), or else of cuvettes or other containers as conventionally used in automated analytical devices.

In its simplest implementation, the experiment is carried out according to the following protocol and, on this basis, it will be easy to imagine many variants.

Colloidal particles having the properties described above are grafted with an antibody specific for an antigen to be assayed. In the interest of clarity, the streptavidin-biotin ligand-receptor couple is considered in this description. Since the streptavidin is grafted onto the particles, the antigen to be detected, by way of example, is a small polyethylene glycol polymer onto which a molecule of biotin has been grafted at both its ends. If a sufficient amount of this antigen is mixed with particles at a fraction by volume of 1% or more, the agglutination in the form of a gel, as expected in the conventional agglutination assay, is visible in a few seconds, or even a few minutes. C* is considered to be the concentration of antigen such that, below this value, the agglutination in the conventional sense is no longer detectable.

The experiment in accordance with the invention consists in mixing particles at a fraction by volume of the order of 0.1% with the antigen at a concentration C far below C*, and referred to as C*/x, in sucking the mixture into a capillary with a rectangular cross section (thickness 20 to 50 μm) and in applying a magnetic field parallel to the axis of the capillary. The field can be applied by virtue of two magnets arranged on either side of the capillary. The field is maintained for two minutes, by way of example, with a strength of at least 500 Gauss. The capillary is then observed with a microscope in order to detect the presence of chains or of aggregates.

The example of the biotin-streptavidin couple thus makes it possible to establish that detection of the aggregates according to the agglutination under magnetic field protocol can occur up to concentrations of antigen of the order of C*/1000.

The method claimed is particularly advantageous for detecting and, where appropriate, quantifying at least one analyte in a microfluid system. In this specific embodiment, it is possible to carry out the magnetic agglutination in a first zone of the microfluid system and the detection in a different zone. This embodiment is in particular advantageously suitable for isolating the permanent chains of particles from the particles which have not undergone agglutination.

A particularly advantageous application of the method according to the invention constitutes multicriteria analysis, for simultaneously assaying several analytes in the same assay.

According to this embodiment, several populations of functionalized magnetic colloidal particles are used. Each population of particles is functionalized with at least one ligand specific for one of the analytes to be detected.

The application of an oscillating magnetic field then leads to the gradual formation of chains made up of particles of the same population, specific for each analyte.

In order to allow them to be distinguished, and therefore to allow the assay to be read, the various populations of magnetic colloidal particles carry a secondary label specific for each analyte to be detected.

A subject of the present invention is also a kit of reagents for detecting at least one analyte in a liquid medium, preferably a biological fluid, characterized in that it comprises at least magnetic colloidal particles functionalized at the surface with at least one ligand specific for said at least one analyte.

BRIEF DESCRIPTION OF THE DRAWINGS

The present invention will be illustrated more clearly by virtue of the following examples, and with regard to the figures which show.

DETAILED DESCRIPTION

The present invention will now be described with reference to the following examples.

EXAMPLE 1

Detection of an Analyte Using Magnetic Colloidal Particles

The example illustrates the detection of a model analyte derived from the biotin/streptavidin high affinity couple and aims to characterize the sensitivity threshold of the method claimed for a given analyte. The analyte consists of biotin, the streptavidin being grafted onto the colloidal particles.

More precisely, the biotinylated analyte is made up of a polyethylene glycol polymer of mass 5000, onto which a molecule of biotin has been grafted at both its ends. These products are commercially available (Shearwater USA).

The streptavidin-grafted superparamagnetic colloidal particles are obtained beforehand. The colloidal particles are obtained according to the procedure published by J. Bibette in J. Magn. and Magn. Mat. V. 122, p. 37 (1993) and F. Leal Calderon, T. Stora, O. Mondain-Monval, P. Poulin and J. Bibette, Phys. Rev. Lett., 72, 2959 (1994) or according to the procedure published by T. Mason and J. Bibette in Phys. Rev. Lett. 77, 3481 (1996) and in WO 97/38787. The polymerization of these particles is obtained according to the protocol described in application FR 2800836. The grafting of the streptavidin to the carboxylic sites is well known to those skilled in the art. Reference may be made to: Molday R S, Dreyer W J, Rembaum A, Yen S P, J Cell Biol 1975 January; 64 (1): 75-88 and Staros J V, Wright R W, Swingle D M, Anal Biochem, 1986, July; 156(1): 220-2.

The agglutination assay under a magnetic field consists in mixing the streptavidin-grafted magnetic colloidal particles with the "PEG-biotin" analytes. The method of detection selected is direct observation under a microscope.

For a given particle fraction by volume Φ, of the order of $10^{-4}$ to $10^{-2}$, the concentration of analytes C is varied so as to detect the limit of sensitivity of the assay.

Figure 1A:
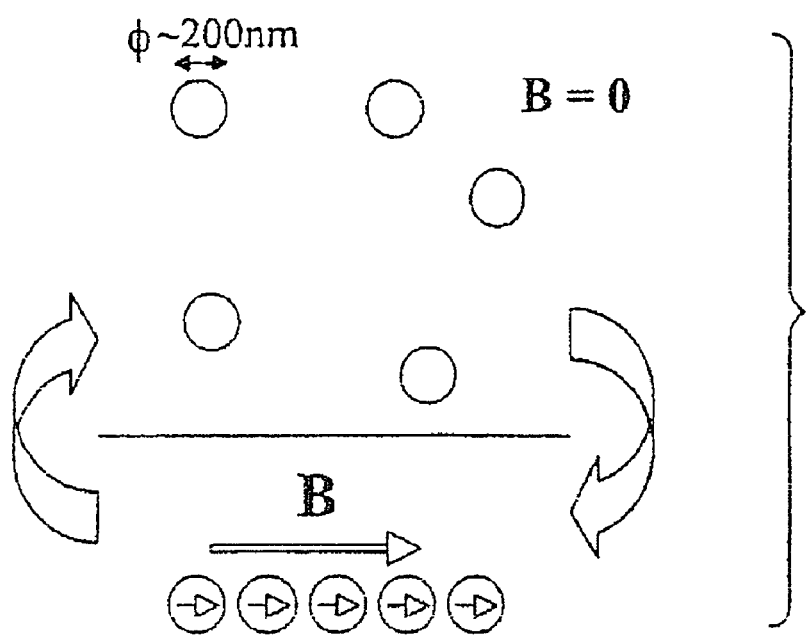
FIG. 1A is a diagram of the principle of formation of lines of magnetic colloidal particles under a magnetic.
Figure 1B:
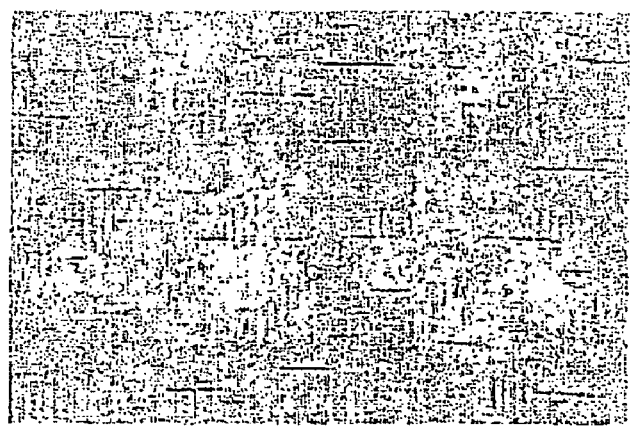
FIG. 1B is a micrograph of the formation of lines of magnetic colloidal particles under a magnetic field.
Figure 2:
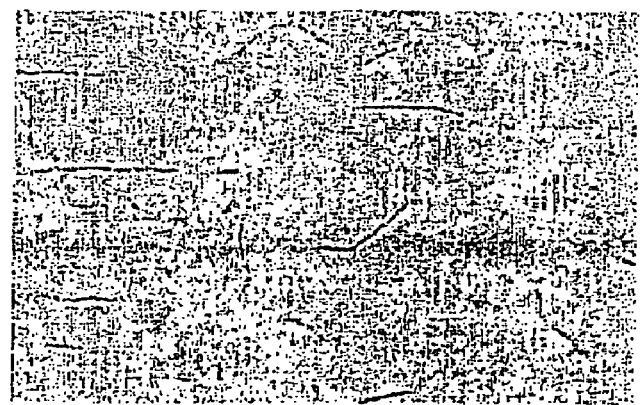
FIG. 2: A micrograph of a solution containing grafted magnetic colloidal particles and biotinylated BSA after the field has been removed.

For each assay, the mixture concerned is sucked into a flat capillary 50 microns in thickness, which is placed between two flat magnets, such that the field produced is greater than approximately 50 mT and parallel to the axis of the capillary. This field is produced using commercial flat magnets. It is applied for approximately 2 minutes and the capillary is observed under a microscope in the absence of magnetic fields. The assay is positive when the presence of chains or of aggregates (see FIG. 2) can be seen under the microscope, and negative when the particles redisperse spontaneously under the action of thermal agitation.

It is found that, according to this embodiment, the assay remains positive down to an analyte concentration of the order of $10^{-9}$ mol/l. By way of comparison, below $10^{-5}$ mol/l, it becomes impossible to carry out a conventional agglutination assay.

Figure 3:
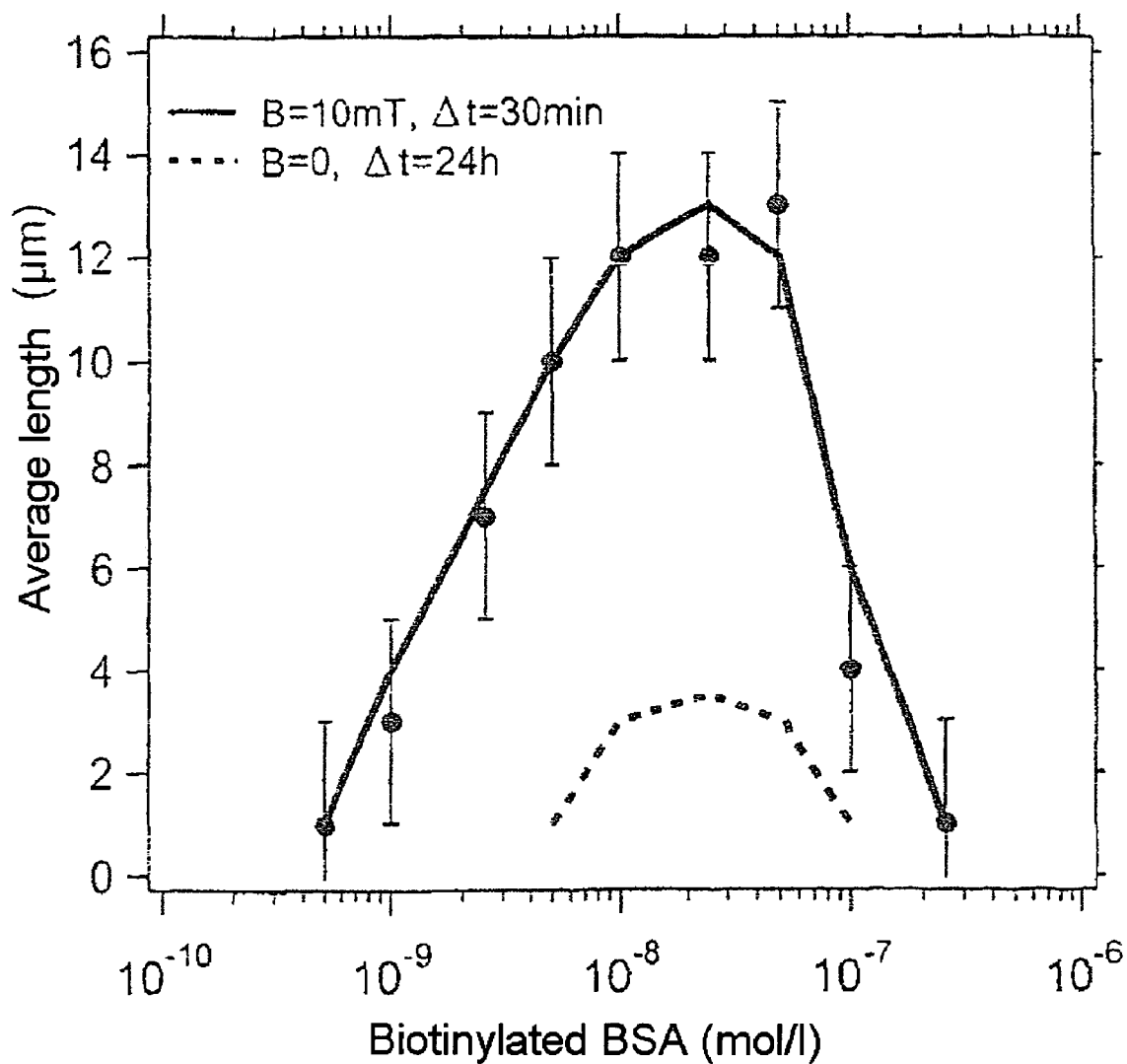
FIG. 3: A graph showing the average length of the lines as a function of the concentration of biotinylated BSA in solution under a field and after the field has been removed.

In a complementary study, the average length of the chains was determined as a function of the concentration of analyte to be assayed (biotinylated BSA, 8 to 12 biotins/BSA). FIG. 3 shows the average length of the chains after 30 minutes in the magnetic field of 10 mT (continuous line) and after 24 hours in the absence of magnetic field (dashed line), as a function of the concentration of biotinylated BSA.

It is noted that application of the magnetic field allows rapid detection of the analyte for analyte concentrations which can be as low as $10^{-9}$ mol/l, or even less, which represents a sensitivity greater than that of the assay currently sold.

In addition, it is noted that the average length of the chains formed increases as a function of the concentration of analyte. Thus, the method of the invention also allows quantitative detection of the analyte to be assayed by virtue of determining the average length of the chains.

EXAMPLE 2

Preparation of Magnetic Colloidal Particles Grafted with Anti-vWF Immunoglobulins G (IgG) and Assaying of von Willebrand Factor 200 μl of a colloidal solution of particles, containing 1% by volume of magnetic colloidal particles (diameter 206 nm, available from Ademtech, France), in a phosphate buffer (20 mM, pH 7.2), are prepared.

In order to activate the particles, 200 μl of aqueous solution of 1-ethyl-3-(3-dimethylaminopropyl)carbodiimide (EDAC) at 0.01 g/l is added to the solution, and the mixture is kept stirring for 20 minutes at 44° C. The excess EDAC is then removed by washing with an aqueous solution of Tween 20 at 0.001%.

Next, the IgGs are grafted onto the colloidal particles by adding 400 μl of colloidal solution of activated particles to 400 μl of IgG solution (1.7 μl of IgG solution at 20 mg/ml in 398 μl of water). The solution is kept stirring for 20 minutes at 44° C., and then for 10 minutes at ambient temperature.

The excess IgG solution is then removed by rinsing with a saturation buffer (glycin-BSA buffer containing 0.001% of Tween 20). The grafted particles thus obtained are then separated by filtration through a 1.2 μm filter.

The grafted particles thus prepared exhibit an antibody grafting of controlled density and orientation. In addition, the grafting is stable, even in the presence of surfactants or of other proteins in the solution. For the von Willebrand factor assay, the Liatest® vVF calibration plasma (STA® vWF Calibrator, available from Diagnostica Stago) containing 200% (2 international units) of von Willebrand factor is used, and the procedure as indicated in the instructions for use of this assay is substantially followed, except that the colloidal solution of grafted magnetic particles is used.

Plasma dilutions at 100%, 1% and 0.1% of von Willebrand factor are prepared with Owren-Koller buffer. The Owren-Koller buffer is used as a control (0%).

Next, 2 volumes of glycin buffer and 3 volumes of the colloidal solution of grafted magnetic particles are added to 1 volume of each of these dilutions.

Figure 4A:
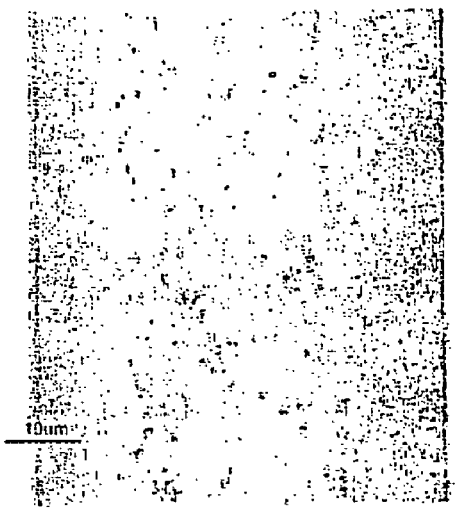
FIG. 4A shows a micrograph of a solution according to Example 2 for a 0% dilution (control)
Figure 4B:
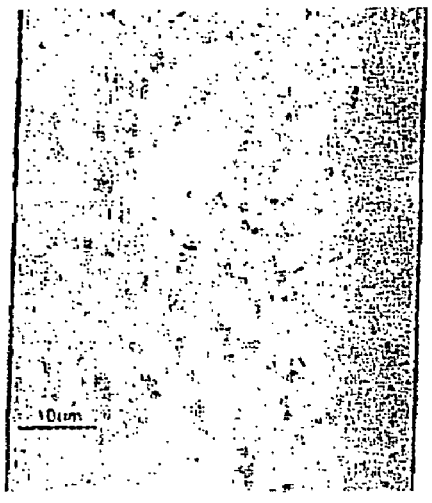
FIG. 4B shows a micrograph of a solution according to Example 2 for a 0.1% dilution.
Figure 4C:
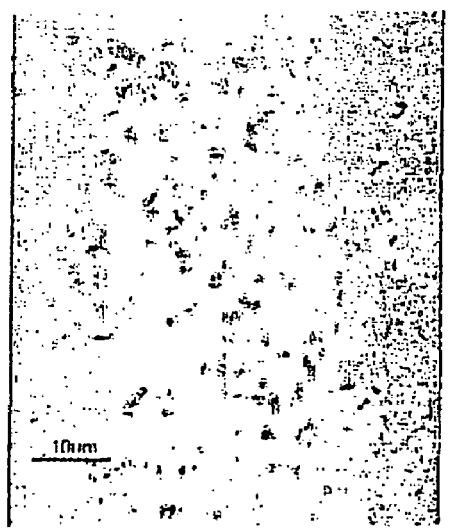
FIG. 4C shows a micrograph of a solution according to Example 2 for a 1% dilution.
Figure 4D:
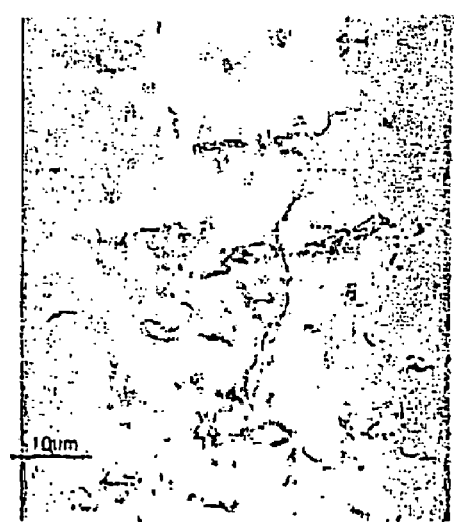
FIG. 4D shows a micrograph of a solution according to Example 2 for a 100% dilution.

The solution obtained is then placed in a square capillary with a 50 μm cross section. The assembly is placed in a magnetic field for 5 minutes at a strength of 70 mT. After the field has been removed, the sample is placed on the platform of an optical microscope. FIGS. 4A, B, C and D show the appearance of the samples under the microscope for the various dilutions studied. It is in particular noted that the method described makes it possible to still visually distinguish a sample at 0.1% of the control (0%). This result is better than the detection threshold of 2% indicated for the LIATEST®.

The invention claimed is:

1. A method for detecting or quantifying at least one analyte in a liquid medium, said method comprising:
   providing magnetic colloidal particles functionalized at the surface with at least one ligand specific for an analyte to be detected or assayed;
   pretreating the medium to be analyzed beforehand in order to make the analyte being sought reactive with respect to at least two molecules of one of its specific ligands, wherein the pretreatment comprises functionalizing the analyte with one of the partners of a high affinity binding couple;
   bringing said particles into contact with said medium to be analyzed;
   applying a continuous magnetic field to said medium, at a strength sufficient to cause said magnetic particles to be structured in the form of chains;
   maintaining said continuous magnetic field for a period of time sufficient to enable coupling or combination of at least one of the analytes concerned with at least two specific ligands present respectively on two consecutive neighboring particles of a chain;
   removing the magnetic field after the period of time sufficient to enable coupling or combination of at least one of the analytes; and
   determining the presence or absence of at least one of the analytes after removing the magnetic field and, where appropriate, a respective concentration of at least one analyte by the presence or absence of permanent chain(s) of magnetic colloidal particles.

2. The method as claimed in claim 1, wherein said particles are superparamagnetic colloidal particles.

3. The method as claimed in claim 2, wherein the superparamagnetic colloidal particles are obtained by coprecipitation of a polymer with an aqueous ferrofluid or by emulsification with a ferrofluid in organic phase.

4. The method as claimed in claim 1, wherein the magnetic colloidal particles are between 5 and 10,000 nm in size.

5. The method as claimed in claim 1, wherein the specific ligands are immobilized at the surface of the particles by absorption interactions, covalent interactions and/or high affinity interactions.

6. The method as claimed in claim 1, wherein the immobilized ligand is one of the two partners of a high affinity binding couple.

7. The method as claimed in claim 6, wherein the ligand is chosen from one of the partners of the couples (poly) carbohydrates/electin, biotin or biotinylated compounds/ avidin or streptavidin, protein receptor and its specific ligand, and haptene/antibody.

8. The method as claimed in claim 1, wherein the immobilized ligand is a compound chosen from peptides, proteins, including glycoproteins, lipoproteins, in free or complex form, immunoglobins, nucleic acids, saccharides, lipids, hormones, receptors, metabolites or other biological substances.

9. The method as claimed in claim 1, wherein the analytes targeted are antigens, antibodies and nucleic acids and/or proteins.

10. The method as claimed in claim 1, for detecting and/or quantifying (an) analyte(s) of the type antibodies to pathogens, antibodies against tumors, antibodies directed against allergens, or autoantibodies.

11. The method as claimed in claim 1, wherein the at least one analyte is an antigen.

12. The method as claimed in claim 1, wherein the magnetic colloidal particles also carry a secondary label.

13. The method as claimed in claim 12, wherein the secondary label can be characterized visually, optically, mechanically and/or electrically.

14. The method as claimed in claim 12, wherein the secondary label is chosen from color pigments and fluorescence agents or phosphore-scence agents.

15. The method as claimed in claim 1, wherein several populations of magnetic colloidal particles functionalized, respectively, with at least one ligand specific for the various analytes to be detected are used.

16. The method as claimed in claim 1, wherein the magnetic field is continuous.

17. The method as claimed in claim 16, wherein the continuous magnetic field is from 5 to 500 mT.

18. The method as claimed in claim 1, wherein the characterization of the chains is carried out directly by visualization under a microscope and/or indirectly by any optical, mechanical or electrical method.

19. The method as claimed in claim 18, wherein the characterization of the chains is carried out by photometry or turbidimetry.

20. The method as claimed in claim 18, wherein the characterization of the chains is carried out by image processing.

21. The method as claimed in claim 20, wherein a CCD camera is used as image-capturing device.

22. The method as claimed in claim 18, wherein a laser is used as light source.

23. The method as claimed in claim 1, wherein the liquid medium is in a microfluid system.

24. The method of claim 1, wherein the magnetic colloidal particles are between 100 and 500 nm in size.

* * * * *